United States Patent [19]

Calderazzo et al.

[11] Patent Number: 4,980,491
[45] Date of Patent: Dec. 25, 1990

[54] PROCESS FOR PRODUCING VANADIUM-ARENES

[75] Inventors: Fausto Calderazzo, Ghezzano; Guido Pampaloni, Pontedera; Francesco Masi, San Donato Milanese; Angelo Moalli, Castelletto Ticino; Renzo Invernizzi, Milan, all of Italy

[73] Assignee: Enichem Anic S.p.A., Palermo, Italy

[21] Appl. No.: 516,267

[22] Filed: Apr. 30, 1990

[30] Foreign Application Priority Data

May 16, 1989 [IT] Italy ............................... 20522 A/89

[51] Int. Cl.$^5$ .............................................. C07F 9/00
[52] U.S. Cl. ..................................................... 556/43
[58] Field of Search .......................................... 556/43

[56] References Cited

U.S. PATENT DOCUMENTS 3,123,571  3/1964  Walker et al. ..................... 252/430
3,231,593  1/1966  Hafner et al. ....................... 260/429
4,526,724  7/1985  Pillsbury ............................. 556/43

OTHER PUBLICATIONS

Silverthorn, Adv. Orgmet. Chem., 13, (1975), pp. 47–137.
Calderazzo, Inorg. Chem., 3, (1964), pp. 810–814.

Primary Examiner—Patrick P. Garvin
Assistant Examiner—Brent Peebles
Attorney, Agent, or Firm—Hedman, Gibson, Costigan & Hoare

[57] ABSTRACT

Vanadium-arenes [V(arene)$_2$] (arene=benzene or mono-, di-, or poly-alkyl-substituted benzene) are obtained, with a high yield, by means of the reduction of a vanadium-arene iodide with zinc, manganese or iron in metal form, or with cobalt di-(cyclopentadienyl).

Vanadium-arenes are useful in the preparation of catalyst components active in ethylene polymerization, or in the copolymerization of ethylene in an alpha-olefin.

6 Claims, No Drawings

PROCESS FOR PRODUCING VANADIUM-ARENES

The present invention relates to a process for producing vanadium-arenes, with a high reaction yield. U.S. patent application Ser. No. 403,681 filed on Sep. 6, 1989 to the same Applicant's name, discloses a solid catalyst component obtained by means of the reaction of a vanadium arene [V(arene)$_2$] and titanium tetrachloride. Such a catalyst component, together with a trialkyl-aluminum, is highly active in the polymerization of ethylene, or in the copolymerization of ethylene with an alpha-olefin C$_3$-C$_{10}$, in the processes carried out in suspension under low pressure and at low temperature, as well as in the processes carried out under high pressure and at a high temperature in a tubular reactor or in autoclave (vessel), as well as in the high-temperature processes carried out in solution.

As regards the preparation of vanadium-arenes, the above cited patent application references to the processes described by E. O. Fischer and H. S. Kogler in Chem. Ber. 90, 250 (1957) and by F. Calderazzo in Inorg. Chem. 3, 810 (1964). Unfortunately these processes make it possible only very poor yields of useful reaction product to be obtained (the overall yields are of the order of 15%), and therefore they are not attractive from an industrial viewpoint.

The present Applicant has found now that vanadium-arenes can be obtained with very good yields by means of the reduction of the corresponding vanadium-arene iodides with special reducing agents. The vanadium-arene iodides can be obtained in their turn by causing vanadium chloride to react with aluminum metal and aluminum trichloride in an arene in order to yield a

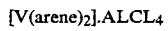

complex, and subsequently treating this complex with an alkali-metal iodide, and this in conformity with the prior art.

In accordance with the above, the present invention relates to a process for producing vanadium-arenes [V(arene)$_2$], wherein "arene" means benzene or mono-, di-, or poly-alkyl-substituted benzene, by means of the reduction of a vanadium-arene iodide [V(arene)$_2$I], characterized in that as the reducing agent an agent is used, which is selected from the group consisting of zinc, manganese or iron in metal form, or with cobalt di(cyclopentadienyl).

In particular, the reduction reaction can be schematized as follows:

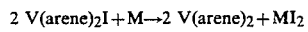

wherein M means zinc, manganese or iron.

In case cobalt-di(cyclopentadienyl) is used as the reducing agent, the reaction can be schematized as follows:

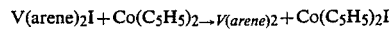

Examples of suitable arenes for the intended purpose are benzene, toluene, p-xylene and mesitylene.

The reaction is advantageously carried out in an inert liquid medium. As inert liquid media, aliphatic hydrocarbons, such as heptane, or cyclic ethers, such as tetrahydrofuran, can be used. The use of cyclic ethers makes it possible higher reaction speeds to be obtained. Good results are also obtained by operating with solvent mixtures constituted by an aliphatic hydrocarbon and a cyclic ether.

The reactants are generally used in equivalent amounts, or a slight excess of the reducing agent over the stoichimetric amount is used.

The reaction temperatures are generally comprised within the range of from 20° C. to 60° C., and the reaction times are comprised within the range of from 15 minutes to 20 hours.

The vanadium-arene can be separated from the reaction mixture by means of traditional methods. However, according to a preferred form of practical embodiment, in which the cyclic ether is used, the separation is carried out by removing the solvent from the reaction mixture by operating at room temperature and under a reduced pressure. The distillation residue is dissolved in a liquid hydrocarbon (preferably heptane) and from the so obtained solution, after a preliminary filtration, the vanadium-arene is crystallized by cooling.

By operating under the above disclosed conditions, the vanadium-arene can be obtained with a yield of up to about 75% by mol, relatively to the vanadium-arene iodide used as the starting product.

As above said, the vanadium-arene iodide can be obtained by means of a process known from the prior art, e.g., the process by F. Calderazzo, as above cited, according to which vanadium chloride, aluminum and aluminum chloride are reacted in an arene in order to yield a

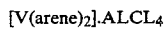

complex, which in its turn is reacted with an alkali-metal iodide, in particular with lithium iodide, in order to yield the vanadium-arene iodide. The first reaction takes place at high temperatures, e.g., of the order of 100°-120° C., and the second reaction takes place at low temperatures (e.g., at about 0° C.) in such a solvent as tetrahydrofuran, from which the reaction product precipitates off. These reactions make it possible vanadium-arene iodide to be obtained with a yield of the order of 70%.

As above said, the vanadium-arenes obtained by means of the process according to the instant invention are useful as components for catalysts in ethylene homo- and co-polymerization. In particular, these vanadium-arenes are reacted with titanium tetrachloride in order to yield a solid catalyst component. This solid component, combined with a trialkyl-aluminum is highly active in the processes of polymerization of ethylene, or of copolymerization of ethylene with an alpha-olefin, carried out by operating in suspension under high pressure and at low temperature, as well as according to the high pressure, high temperature technology in a tubular reactor or in an autoclave (vessel), as well as in the high-temperature processes carried out in solution.

The following experimental examples are reported in order to better illustrate the invention.

EXAMPLE 1

Preparation of vanadium-mesitylene according to the reaction:

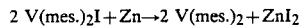

0.68 g of zinc powder (10.4 mmol), 100 ml of anhydrous tetrahydrofuran and 7.27 g of vanadium-mesitylene iodide [V(mes.)$_2$I]—with this latter being obtained according to as described by F. Calderazzo in Inorganic Chemistry, 3, page 810 (1964)—are charged to a test tube of 250 ml of capacity equipped with a side pipe fitting, in the same order as said and under an inert blanketing atmosphere.

The so obtained, light-brown-coloured suspension is kept with stirring at 25° C. for a 15-hours time, and at the end of this time period a suspension is obtained, which is constituted by a gray solid in a red solution. Tetrahydrofuran is removed by operating under reduced pressure and at room temperature (20°–25° C.), and the solid residue is suspended again in 50 ml of anhydrous n-heptane. The red-brown-coloured suspension is filtered and the solid on the filter is washed five times, each time with 10 ml of anhydrous n-heptane. The red, clear heptane solution obtained is concentrated to a volume of about 40 ml. The so obtained red crystals are rapidly separated at low temperature by decantation of the mother liquors, and are dried under vacuum at room temperature.

The yield of vanadium-mesitylene [V(mes.)$_2$] is hence of 70.6% by mol, relatively to the vanadium-mesitylene iodide used as the starting product.

EXAMPLE 2

Preparation of vanadium-mesitylene according to the reaction:

$$V(mes.)_2I + Co(C_5H_5)_2 \rightarrow Co(C_5H_5)_2I + V(mes.)_2$$

2.24 g of Co(C$_5$H$_5$)$_2$ (11.9 mmol), 50 ml of anhydrous tetrahydrofuran and 5.03 g of vanadium-mesitylene iodide (12 mmol)—with this latter being obtained according to the process as described by F. Calderazzo in Inorganic Chemistry, 3, page 810 (1964)—are charged to a test tube of 100 ml of capacity equipped with a side pipe fitting, in the same order as said and under an inert blanketing atmosphere.

After a 1-hour stirring at room temperature, a suspension is obtained, which is constituted by a yellow solid in a red solution. Tetrahydrofuran is removed by operating under reduced pressure and at room temperature (20°–25° C.), and the solid residue is suspended again in 50 ml of anhydrous n-heptane. The suspension is filtered and the solid remaining on the filter is washed three times, each time with 10 ml of anhydrous n-heptane. The red, clear heptane solution obtained is concentrated to a volume of about −30 ml, is cooled down to about −78° C. and then is left standing overnight at this temperature. The so obtained red crystals are rapidly separated at low temperature by decantation of the mother liquors, and are dried under vacuum at room temperature.

2.62 g of vanadium-mesitylene is obtained, with a yield of 75.1% by mol, relatively to the vanadium-mesitylene iodide used as the starting product.

EXAMPLE 3

Preparation of vanadium-mesitylene according to the reaction:

$$2 V(mes.)_2I + Fe \rightarrow 2 V(mes.)_2 + FeI_2$$

4.29 g of vanadium-mesitylene iodide (10.2 mmol)—with this latter being obtained according to as described by F. Calderazzo in Inorganic Chemistry, 3, page 810 (1964)—50 ml of anhydrous tetrahydrofuran and 0.282 g of iron powder (5.05 mmol), are charged to a test tube of 250 ml of capacity, in the same order as said and under an inert blanketing atmosphere.

The so obtained, light-brown-coloured suspension is kept with stirring at room temperature for a 15-hours time. At the end of this time period a suspension of reddish colour is obtained, which is concentrated to dryness by operating under reduced pressure and at room temperature (20°–25° C.), and the solid residue is suspended again in 50 ml of anhydrous n-heptane. The suspension is filtered at 70°–80° C. and the solid on the filter is washed three times, each time with 10 ml of anhydrous n-heptane. The red, clear heptane solution obtained is cooled to about −78° C. and is left standing overnight at this temperature. The so obtained red crystals are rapidly separated at low temperature from the mother liquors, and are dried under vacuum at room temperature.

2.25 g of vanadium-mesitylene is obtained, with a yield of 75% by mol, relatively to the vanadium-mesitylene iodide used as the starting product.

EXAMPLE 4

Preparation of vanadium-mesitylene according to the reaction:

$$2 V(mes.)_2I + Mn \rightarrow 2 V(mes.)_2 + MnI_2$$

0.228 g of manganese powder (4.15 mmol), 50 ml of anhydrous tetrahydrofuran and 3.45 g of vanadium-mesitylene iodide—with this latter being prepared according to as described by F. Calderazzo in Inorganic Chemistry, 3, page 810 (1964)—are charged to a previously dried test tube of 250 ml of capacity, in the same order as said and under an inert blanketing atmosphere.

The so obtained suspension is kept with stirring at room temperature (20°–25° C.) for a 15-hours time. The resulting suspension, containing a gray-brown solid in a red solution is concentrated to dryness by operating under reduced pressure and at room temperature. The solid residue is suspended again in 50 ml of anhydrous n-heptane. The suspension is heated for 30 minutes at 70°–80° C. and the solid is separated by high-temperature filtration. The solid residue on the filter is washed three times, each time with 5 ml of anhydrous n-heptane. The red, clear heptane solution obtained is cooled to about −78° C. and is left standing at this temperature for 5 hours. The so obtained red crystals are rapidly separated at low temperature from the mother liquors, and are dried under vacuum at room temperature (20°–25° C.).

1.544 g of vanadium-mesitylene is obtained, with a yield of 64.2% by mol, relatively to the vanadium-mesitylene iodide used as the starting product.

EXAMPLE 5

Preparation of vanadium-mesitylene according to the reaction:

$$2 V(mes.)_2I + Zn \rightarrow 2 V(mes.)_2 + ZnI_2$$

0.07 g of zinc powder (1.07 mmol), 20 ml of anhydrous n-heptane and 0.805 g of vanadium-mesitylene iodide—with this latter being obtained according to as described by F. Calderazzo in Inorganic Chemistry, 3, page 810 (1964)—are charged to a test tube of 50 ml of capacity equipped with a side pipe fitting, in the same order as said and under an inert blanketing atmosphere.

The reaction mixture is kept stirred for 6 hours at 60° C., and at the end of this time period a suspension is obtained, which is constituted by a gray-brown solid in a red solution. The suspension is filtered and the residual solid on the filter is washed three times, each time with 10 ml of anhydrous n-heptane. The heptane solution is concentrated to a volume of about 10 ml, is cooled down to about −78° C., and is kept at this temperature for 4 hours. The so obtained red crystals are rapidly separated at low temperature and are dried under vacuum at room temperature.

The yield of so obtained vanadium-mesitylene is hence of 50% by mol, relatively to the vanadium-mesitylene iodide used as the starting product.

EXAMPLE 6

Preparation of vanadium-mesitylene according to the reaction:

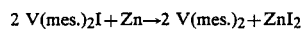

1.3 g of zinc powder (19.88 mmol), 200 ml of anhydrous n-heptane 2 ml of anhydrous tetrahydrofuran and 14 g of vanadium-mesitylene iodide (33.4 mmol)—with this latter being obtained according to as described by F. Calderazzo in Inorganic Chemistry, 3 page 810 (1964) —are charged to a test tube of 500 ml of capacity equipped with a side pipe fitting, in the same order as said and under an inert blanketing atmosphere.

The reaction mixture is kept stirred for 6 hours at 60° C., and at this end of this time period a suspension is obtained, which is constituted by a gray solid in a red solution. The suspension is filtered and the residual solid on the filter is washed four times, each time with 30 ml of anhydrous n-heptane. The heptane solution is concentrated to a volume of about 50 ml, is cooled down to about −78° C., and is left standing at this temperature for 4 hours. The so obtained red crystals are rapidly separated at low temperature and are dried under vacuum.

6.03 g of vanadium-mesitylene (20.7 mmol) is obtained, with a yield of 62% by mol, relatively to the vanadium-mesitylene iodide used as the starting product.

We claim:

1. Process for producing vanadium-arenes [V(arene)$_2$], wherein "arene" means benzene or mono-, di-, or poly-alkyl-substituted benzene, by means of the reduction of a vanadium-arene iodide [V(arene)$_2$I], characterized in that as the reducing agent an agent is used, which is selected from the group consisting of zinc, manganese or iron in metal form, or with cobalt di(cyclopentadienyl).

2. Process according to claim 1, characterized in that the arene, in the vanadium-arene, is selected from the group consisting of benzene, toluene, p-xylene and mesitylene.

3. Process according to claim 1, characterized in that the reaction is carried out in an inert liquid medium selected from the group consisting of the aliphatic hydrocarbons and the cyclic ethers, or relevant mixtures thereof.

4. Process according to claim 3, characterized in that said liquid medium is selected from among heptane, tetrahydrofuran, or relevant mixtures thereof.

5. Process according to claim 1, characterized in that stoichiometric amounts of the reactants, or a slight excess of the reducing agent, are used.

6. Process according to claim 1, characterized in that the process is carried out at a temperature comprised within the range of from 20° C. to 60° C., for a time comprised within the range of from 15 minutes to 20 hours.

* * * * *